US005656749A

United States Patent [19]
Spindel et al.

[11] Patent Number: 5,656,749
[45] Date of Patent: Aug. 12, 1997

[54] NUCLEIC ACIDS ENCODING RECEPTORS FOR BOMBESIN-LIKE PEPTIDES

[75] Inventors: Eliot R. Spindel, Lake Oswegor; Srinivasa Nagalla; Brenda Barry, both of Portland, all of Oreg.

[73] Assignee: Oregon Regional Primate Research Center, Beaverton, Oreg.

[21] Appl. No.: 279,590

[22] Filed: Jul. 22, 1994

[51] Int. Cl.$^6$ ....................................... C12N 15/12
[52] U.S. Cl. ................. 536/23.5; 435/69.1; 435/320.1; 435/252.3; 435/254.11; 435/325
[58] Field of Search .................. 536/23.1, 23.5; 435/240.1, 320.1, 252.3, 254.11, 240.2, 69.1

[56] References Cited

PUBLICATIONS

Battey et al., PNAS, vol. 88, pp. 395–399, 1991.
Shirakawa et al., Am. J. Physiol., vol. 249 (6Pt 1) pp. G668–673, 1985.
Battery and Wada, "Two distinct receptor subtypes for mammalian bombesin–like peptides," TINS, 114:524–528, 1991.
Fathi, et al., "BRS–3: A Novel Bombesin Receptor Subtype Selectively Expressed in Testis and Lung Carcinoma Cells," The Journal of Biological Chemistry, 268:5979–5984, 1993.
Giladi, et al., "Molecular Cloning and Characterization of Receptors for the Mammalian Bombesin–Like Peptides," Journal of Molecular Neuroscience, 4:41–54, 1993.
Giladi and Spindel, "Simple Luminometric Assay to Detect Phosphoinositol–Linked Receptor Expression in *Xenopus* Oocytes," BioTechniques, 10:744–747, 1991.
Gorbulev, et al., "Molecular cloning of a new bombesin receptor subtype expressed in uterus during pregnancy," Eur. J. BioChem, 208:405–410, 1992.

Julius, et al., "Molecular Characterization of a Functional cDNA Encoding the Serotonin 1c Receptor," Science, 241–558–564, 1988.
Moody, T.W., et al., "Characterization of Receptors for Bombesin/Gastrin–Releasing Peptide in Human and Murine Cells," Method Enzymol, 168:481–493, 1989.
Nagalla, et al., "Gastrin–releasing Peptide (GRP) Is Not Mammalian Bombesin," The Journal of Biological Chemistry, 267:6916–6922, 1992.
Spindel, et al., "Cloning and Functional Characterization of a Complementary DNA Encoding the Murine Fibroblast Bombesin . . . ," Molecular Endocrinology, 4:1956–1963, 1990.
Sandberg, et al., "Calcium mobilization by angiotensin II and neurotransmitter receptors expressed in *Xenopus Laevis* oocytes," FEBS Lett., 241:177–180, 1988.
Von Schrenck, et al., "Neuromedian B receptor in esophagus: evidence for subtypes of bombesin receptors," Bombesin Receptor Subtypes, 256:G–747–G758, 1989.
Wada, et al., "cDNA Cloning, Characterization, and Brain Region–Specific Expression of a Neuromedian–B–Preferring Bombesin Receptor," Neuron, 6:421–430, 1991.
Wada, et a., "Comparison of Gene Expression for Two Distinct Bombesin Receptor Subtypes in Postnatal Rat Central Nervous System," Molecular and Cellular Neurosciences, 3:446–460, 1992.

*Primary Examiner*—Stephen Walsh
*Assistant Examiner*—Sally P. Teng
*Attorney, Agent, or Firm*—Fish & Richardson P.C.

[57] ABSTRACT

Pure nucleic acids encoding novel receptors for bombesin-like peptides, the novel receptors themselves, and their antibodies. Also disclosed is a method of screening for a compound capable of interacting with any of these novel receptors.

12 Claims, 2 Drawing Sheets

```
                                                                v230
                              v220              ProTyrIleValProLeuSerIleIleSerAlaTyrTyrPhe
             v210             ProLeuIleCysPheLeuValPheTyrIleValProLeuSerIleIleSerAlaTyrTyrPhe
ProTyrProValSerGluLysIleLeuGlnGluThrHisSerLeuIleCysPheLeuValPheTyrIleValProLeuSerIleIleSerAlaTyrTyrPhe
CCATATCCAGTCTCTGAAAAGATTCTGCAAGAGACACATTCCTAATATGCTTCCTGGTATTCCTACATTCTACATTTCTGCATATTACT
                 ^820                            ^840                           ^860                     ^880
                                            v260
           v240                             ArgLysArgValAlaLys
LeuIleAlaLysThrLeuTyrLysSerThrPheAsnMetProAlaGluGluHisThrHisAlaArgLysGlnIleIleGluSerArgLysArgValAlaLys
TCCTTATTGCAAAACCCTGTACAAAAGTACTTTCAACATGCCTGCTGAAGAGCACACTCACGCCCGAAAACAGATAGAATCGCGCAAACGAGTGGCAAA
                 ^920                           ^940                            ^960                     ^980
                                                                                              v300
                                                    v290                                      AsnSer
ThrValLeuValAlaLeuPheAlaValCysTrpLeuProAsnHisMetLeuTyrLeuTyrArgSerPheThrTyrHisSerAlaValAsnSer
AACTGTGCTGCTATTGCTTGTCTGGTGGCCTATTTGCCTAACCACATGCTCTACTTGTATCGATCCTTCACATATCACTCCGCAGTGAATTCC
                 ^1020                          ^1040                           ^1060                    ^1080
                                                                          v330
           v310                           v320                            SerArgSerPheArg
SerAlaPheHisLeuSerAlaThrIlePheAlaAlaArgValLeuAlaLeuAlaArgAsnSerCysValAsnProPheAlaLeuTyrTrpLeuSerArgSerPheArg
TCTGCGTTTCACCTGTCAGCACGATTTTTGCGGCGA

NUCLEIC ACIDS ENCODING RECEPTORS FOR BOMBESIN-LIKE PEPTIDES

STATEMENT AS TO FEDERALLY SPONSORED RESEARCH

This invention was made with support from the National Institute of Health (Grant No. R01-CA39237). Accordingly, the U.S. government may have certain rights in the invention.

FIELD OF THE INVENTION

The present invention relates generally to the manipulation of genetic materials, and, more particularly, to recombinant DNA procedures which make possible the identification of novel DNA sequences and polypeptides encoded thereby.

BACKGROUND OF THE INVENTION

Bombesin, a tetradecapeptide amide first isolated from the skin of the frog Bombina bombina, is a potent mitogen for mouse Swiss 3T3 fibroblast cells. It also stimulates secretion for guinea pig pancreatic acini. Bombesin-like peptides are produced and secreted by human small cell lung cancer cells and exogenously added bombesin-like peptides can stimulate the growth of human SCLC cells in vitro. Two examples of bombesin-like peptides are gastrin releasing peptide (GRP) and neuromedin B (NMB).

GRP is a 27 amino acid peptide amide and was first isolated from the porcine gut. The C-terminal amino acid sequence of GRP is almost identical to that of bombesin. NMB, on the other hand, is a decapeptide amide, the structure of which is almost identical to the last ten amino acids in the C-terminal region of GRP. Both GRP and NMB share high amino acid sequence homology with bombesin and indeed possess bombesin-like properties. Other bombesin-like peptides include litorin and neuromedin C (NMC).

Recent structure-function and DNA cloning studies demonstrate that at least two classes of receptors mediate the action of bombesin-like peptides. One class, the GRP preferring subtype (GRP receptor), has a high affinity for GRP and a low affinity for NMB, whereas the other class, the NMB-preferring subtype (NMB receptor), has a high affinity for NMB and lower affinity for GRP. Both classes of receptors are widely present both in the central nervous system and in the gastrointestinal tract. A third receptor class, the BRS-3 receptor, has recently been found in both rat testes and pregnant uteruses. Unlike the GRP and NMB receptors, none of the presently known bombesin-like peptide binds with high affinity ($K_d$<25 nM) to the BRS-3 receptor.

SUMMARY OF THE INVENTION

We have discovered novel genes which code for receptors capable of binding to bombesin-like peptides. The term "bombesin-like peptide" used here and below refers to a peptide capable of binding with a $K_d$ less than 1 µM to either the GRP receptor, the NMB receptor, the BRS-3 receptor, or to any other bombesin receptor subtypes such as the BB4 and BB5 receptors described below. Examples of bombesin-like peptides include, but are not limited to, bombesin, GRP, NMB, NMC, BB4 and BB5.

Accordingly, in one aspect, the invention features a pure nucleic acid (for example, genomic DNA, cDNA, or RNA) encoding a receptor for a bombesin-like peptide, the receptor including SEQ ID NO: 2, SEQ ID NO: 4, or SEQ ID NO: 6 (e.g., either as the entirety of the receptor or as a fragment thereof). In other words, a pure nucleic acid which encodes a receptor for a bobmesin-like peptide and includes SEQ ID NO: 1, SEQ ID NO: 3, or SEQ ID NO: 5; or a degenerate variant thereof embodies an aspect of this invention.

The invention also features a pure nucleic acid which (i) is capable of hybridizing to SEQ ID NO: 1, SEQ ID 5 NO: 3, or SEQ ID NO: 5 under a high- or a low-stringency hybridization condition; and (ii) encodes a receptor protein for a bombesin-like peptide. By "low-stringency hybridization condition" is meant: prehybridization in 25% formamide, 5× SSC, 25 mM potassium phosphate buffer (pH 7.4), 5× Denhardt's, and 50 µg/ml denatured salmon sperm DNA for 4–12 hours at 37° C. which is followed by hybridization for 12–24 hours at 37° C. and washing in 2× SSC containing 0.1% SDS, at 42° C.; or an equivalent thereof. By "high-stringency hybridization condition" is meant: prehybridization in 50% formamide, 5× SSC, 25 mM potassium phosphate buffer (pH 7.4), 5× Denhardt's, and 50 µg/ml denatured salmon sperm DNA for 4–12 hours at 37° C., which is followed by hybridization for 12–24 hours at 37° C. and washing in 2× SSC containing 0.1% SDS, at 55° C.; or an equivalent thereof. E.g., see Sambrook, et al. Molecular Cloning, A Laboratory Manual, 2nd Ed. Cold Spring Harbor Laboratory Press, New York (1989), hereby incorporated by reference.

In related aspects, a cell containing one of the nucleic acids mentioned above, and a vector which includes such a nucleic acid and is capable of directing expression of the peptide encoded by that nucleic acid in a vector-containing cell are also within the scope of this invention.

Other embodiments include a pure receptor protein encoded by a nucleic acid of this invention which is capable of binding to a bombesin-like peptide, and a pure antibody which is specific for such a receptor protein.

In another aspect, this invention features a method of screening for a compound capable of interacting with a receptor protein for a bombesin-like peptide, the method comprising the steps of: (i) providing a cell which expresses a receptor protein of this invention (e.g., a native cell expressing the receptor obtained from the brain tissue, a frog egg into which mRNA encoding the receptor is introduced, or a host cells into which DNA encoding the receptor protein is introduced for expression); (ii) contacting the compound with the receptor protein expressed by the cell; and (iii) detecting an interaction, if any, between the compound and the receptor protein (e.g., binding or any biochemical response as a result of the binding).

By "pure nucleic acid" is meant a nucleic acid that is free or substantially free (i.e., at least 60% by weight free) of the DNA or RNA sequences which, in the naturally-occurring genome of the organism from which the nucleic acid of the invention is derived, flank it. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. Chemically synthesized nucleic acids are also encompassed.

By "protein" is meant any chain of amino acids, regardless of length or post-translational modification (e.g., glycosylation or phosphorylation).

By "pure receptor protein" or "pure antibody" is meant a receptor protein or antibody which has been substantially separated from components which naturally accompany it, i.e., it is at least 60%, by weight, free from the proteins and naturally-occurring organic molecules with which it is naturally associated. A pure protein (i.e., a receptor protein or an antibody of this invention) may be obtained, for example, by extraction from a natural source, by expression of a recombinant nucleic acid, or by chemical synthesis. Purity can be measured by any appropriate method, e.g., those described in column chromatography, polyacrylamide gel electrophoresis, or by HPLC analysis.

Other features and advantages of the invention will be apparent from the following description and from the claims.

BRIEF DESCRIPTION OF THE DRAWINGS

The drawings are first briefly described.

FIG. 1 is a nucleotide sequence (SEQ ID NO:1) encoding the frog BB4 receptor; the encoded amino acid sequence (SEQ ID NO:2) is also shown.

DETAILED DESCRIPTION OF THE INVENTION

Figure 2:
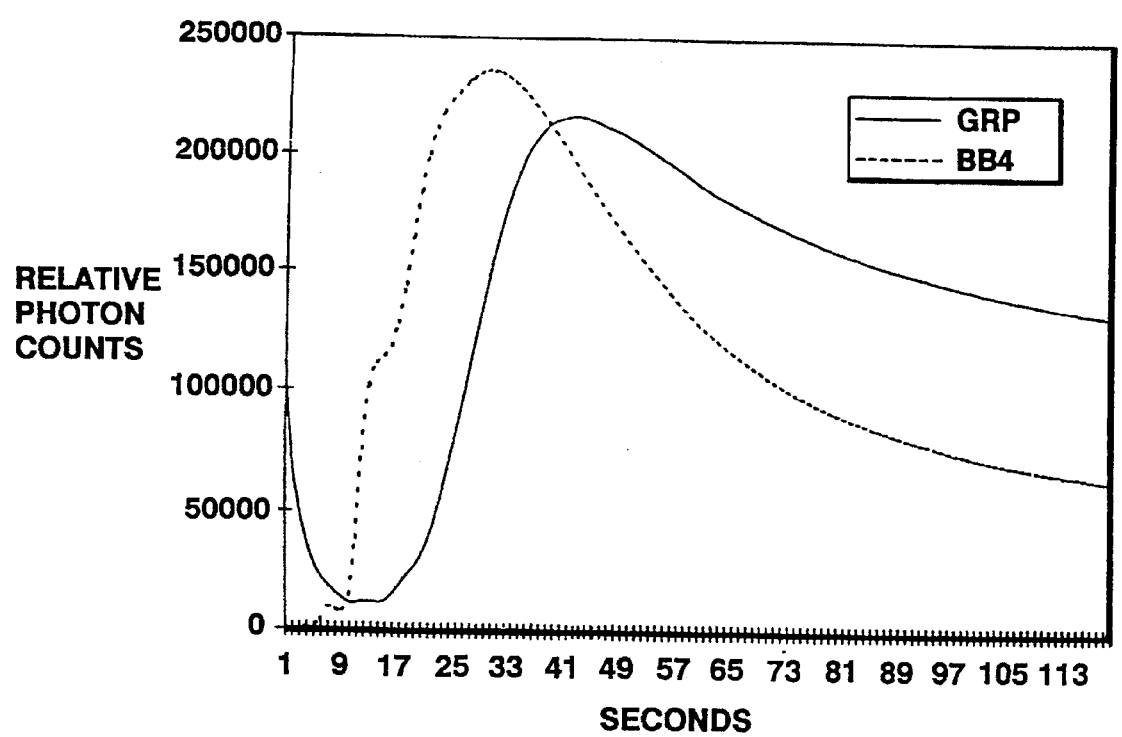
FIG. 2 is a graph showing the responses to exogenous bombesin of Xenopus oocytes injected respectively with RNA's encoding the human GRP receptor and the frog BB4 receptor.

Insertion of a DNA sequence of this invention into a vector, introduction of the recombinant vector thus obtained into a host cell, and subsequent expression of a receptor protein encoded by the inserted DNA sequence can be performed to produce that receptor protein. Such techniques are well known to a person of ordinary skill in the art, and in any event can be found in the literature, e.g., Sambrook, et al. Molecular Cloning, A Laboratory Manual, 2nd Ed. Cold Spring Harbor Laboratory Press, New York (1989), hereby incorporated by reference. Note that all nucleic acid sequences of this invention can be readily prepared by a person of ordinary skill in the art employing one or more the DNA sequences disclosed herein.

A receptor of this invention or its fragment (produced recombinantly, synthetically, or by conventional purification methods) can be used to generate an antibody (monoclonal or polyclonal) to be used as a diagnostic tool for detecting that receptor on cells from a given tissue, since the presence or expression level of that receptor may be related to cancer or other disorders. Of course, such an antibody can also be generated using a peptide fragment (e.g., a fragment of that receptor) which has at least one antigenic determinant that is immunologically reactive with an antigenic determinant of that receptor. Methods of generating and collecting such an antibody are well known in the art. For example, see Harlow et al., Antibodies—Laboratory Manual (1988, Cold Spring Harbor Laboratory), which is hereby incorporated by reference.

Conversely, any positively identified cells can be used to screen for compounds (e.g., a synthetic compound or the native ligand of that receptor) which interact with that receptor in various ways. As an example, bombesin-like peptides are produced and secreted by human small cell lung cancer cells (see BACKGROUND OF THE INVENTION above). Thus, some of the positively identified compounds (agonists or antagonists) can be used in the diagnosis or treatment of small cell lung cancer.

One way of detecting an interaction between a compound and the receptor of this invention is to monitor changes in intracellular calcium, as demonstrated in an actual example shown below. Alternatively, binding assays can be performed in screening for compounds which interact with the receptor. For experimental details, see von Schrenck T., et al. Am. J. Physiol. 1989; 256:G747–G758; and Moody T. W., et al., Methods Enzymol. 1989; 168:481–493, both of which are hereby incorporated by reference.

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever.

Identification of novel receptors for bombesin-like peptides

The rat, mouse, and human GRP receptors and the human and rat NMB receptors were aligned in a manner described in Spindel, et al., Recent. Prog. Horm. Res. 1993; 48:365, 380–81, which is hereby incorporated by reference. This multiple alignment indicated certain conserved regions, based on which PCR primers and probes were prepared as tools used to look for novel receptors for bombesin-like peptides. More specifically, the following primers/probes were prepared: AT(ACT) CA(AG) CTI ACI TCI GTI GGI GTI TCI GT (SEQ ID NO: 7); (GA)TA IAG IGC (GA)AA IGG (AG)TT IAC (GA)CA IGA (GA)TT (SEQ ID NO: 8); (AC)G(ACGT) AA(AG) (AC)G(ACGT) (CT)T(ACGT) GC(ACGT) AA (SEQ ID NO: 9); and CC(ACGT) AC(GA) AA(ACGT) AC(ACGT) A(GA)(ACGT) AC (SEQ ID NO: 10). All primers/probes are written 5' to 3' mixed residues are shown in parentheses, and the symbol "I" denotes deoxyinosine.

Total RNA was then prepared by homogenization of frog brain (Bombina orientalis) in guanidine thiocyanate followed by centrifugation through CsCl. 5 µg total RNA was reverse transcribed with 25 pmole oligo(dT$^{18}$), 200 units of M-MLV reverse transcriptase (GIBCO-BRL, Gaithersburg, Md.), 5× buffer (250 mM Tris-HCl, pH 8.3; 375 mM KCl, 15 mM MgCl$_2$, 50 mM DTT, 2.5 mM dNTP's) in 20 µl total volume at 37° C. for 1 hour. The entire reverse transcription was used in a 100 µl PCR reaction using 100 pmoles of SEQ ID NO: 7 and 100 pmoles of SEQ ID NO: 8. PCR conditions consisted of one cycle at 92° C.×2 min, 55° C.×2 min, 72° C.×3 min for second strand synthesis, followed by 35 cycles of 92° C.×40 sec, 55° C.×1 min, 72° C.×2 min. A 20 µl-aliquot of this reaction was separated on a 1% agarose gel, transferred to a Nylon membrane and hybridized to two $^{32}$P-end labelled internal oligonucleotide probes (SEQ ID NO: 9 and SEQ ID NO: 10). The hybridizing product was subcloned into PGEM-T vector (Promega, Madison, Wis.) and sequenced as described in Nagalla, et al., J. Biol. Chem. 1992; 267:6916–22, which is hereby incorporated by reference.

Sequence analysis of multiple clones revealed a nucleotide sequence corresponding to position 585-position 1178 of SEQ ID NO: 1, which encoded amino acid sequence corresponding to position 132-position 329 of SEQ ID NO: 2. Both SEQ ID NO: 1 and 2 are shown in FIG. 1. The homology of the encoded amino acid sequence with the GRP, NMB and BRS-3 receptors was analyzed. The encoded amino acid sequence showed a 70.7% homology with the BRS-3 receptor, a 61.1% homology with the GRP receptor, and a 51.1% homology with the NMB receptor. These results suggested that this newly discovered encoded amino acid sequence represented a new receptor subtype, which is designated as frog BB4 receptor. To prove that this receptor was not the GRP or NMB receptor, other clones were isolated from frog stomach, brain and skin mRNA that had higher (>80% homology) with their mammalian counterparts.

A cDNA library was next constructed from B. orientalis brain in the vector λZAP II (Stratagene, Inc., La Jolla, Calif.) using reagents and protocols provided by the supplier. To screen the cDNA library, a $^{32}$P-labeled cRNA probe was prepared from the nucleotide sequence which corresponds to position 585-position 1178 of SEQ ID NO: 1 using the T7 promoter in the PGEM-T vector. A hybridizing clone was isolated and found to encode the full coding sequence of the Bombina orientalis BB4 receptor. See SEQ ID NO: 1 and 2 in FIG. 1. As will be set forth below, functional studies showed that frog BB4 receptor potently responded to bombesin, suggesting that this new receptor represents the prototype receptor for the bombesin/ranatensin branch of the bombesin-like peptides and is different from the BRS-3 receptor which does not respond to bombesin.

The cDNA encoding the frog BB4 receptor was then used to screen a monkey brain cDNA library (purchased from Clontech, Inc., Palo Alto, Calif.) at low stringency (25% formamide, 5× SSC, 37° C. with washing at 50° C. in 2× SSC). Multiple hybridizing clones were isolated. Sequence analysis of the clones revealed two subtypes with partial sequences: monkey BB4 (SEQ ID NO: 3) and monkey BB5 (SEQ ID NO: 5), which encode SEQ ID NO: 4 and SEQ ID NO: 6, respectively. Monkey BB4 appears highly homologous to frog BB4, i.e., an 88.1% homology in the 84 amino acid overlap. SEQ ID NO: 3, 4, 5 and 6 are shown below:

CAGACATCTG ACGCGGTGTT GAAGACGTGC GGCAAAGCTG TTTGTGTTTG GATTATCTCC ATGC- TACTTG CTGCCCCTGA GGCAGTGTTT TCGGATTTGT ATGAATTCAC CAGCCCTGAC AAGAATATGT CCT- TCAAAAC ATGTGCCCCT TATCCTGTTT CTGAAAAGCT ACTGCAAGAG ACACATTCGC TGATGTGCTT CTTAGT- GTTC TATATTATTC CCTTGTCTAT TATCTCCGCC TAC- TACTTCC TC                SEQ ID NO: 3

Gln Thr Ser Asp Ala Val Leu Lys Thr Cys Gly Lys Ala Val Cys Val Trp Ile Ile Ser Met Leu Leu Ala Ala Pro Glu Ala Val Phe Ser Asp Leu Tyr Glu Phe Thr Ser Pro Asp Lys Asn Met Ser Phe Lys Thr Cys Ala Pro Tyr Pro Val Ser Glu Lys Leu Leu Gln Glu Thr His Ser Leu Met Cys Phe Leu Val Phe Tyr Ile Ile Pro Leu Ser Ile Ile Ser Ala Tyr Tyr Phe Leu                SEQ ID NO: 4

CAGACCTCAG ATGCTGTGCT GAAGACCTGT GCCAAAGCTG GTGGCATCTG GATCATGGCT ATGATATTTG CTCTGCCAGA GGCTATATTC TCAAATG- TAT ACACTTTCCA AGGTCCTAAC AGAAACGTAA CATTTGAATC CTGTAACTCC TACCCTATCT CTGAGAG- GCT TTTGCAGGAA ATACATTCTC TGTTGTGTTT CTTG- GTGTTC TACATTATCC CGCTCTCGAT TATCTCCGCC TATTACTTCC                SEQ ID NO: 5

Gln Thr Ser Asp Ala Val Leu Lys Thr Cys Ala Lys Ala Gly Gly Ile Trp Ile Met Ala Met Ile Phe Ala Leu Pro Glu Ala Ile Phe Ser Asn Val Tyr Thr Phe Gln Gly Pro Asn Arg Asn Val Thr Phe Glu Ser Cys Asn Ser Tyr Pro Ile Ser GluArg Leu Leu Gln Glu Ile His Ser Leu Leu Cys Phe Leu Val Phe Tyr Ile Ile Pro Leu Ser Ile Ile Ser Ala Tyr Tyr Phe                SEQ ID NO: 6

Function studies (changes in intracellular calcium)

To prepare the receptor RNA for injection into Xenopus oocytes, the linearized cDNA encoding frog BB4 receptor, was phenol extracted, ethanol precipitated, and then transcribed with T7 or T3 RNA polymerase. Transcription reactions were carried out in a 50–100 µl volume containing 5–20 µg DNA template, 40 mM Tris (pH 7.9), 7 mM MgCl$_2$, 10 mM DTT, 2 mM spermidine, 10 mM NaCl, 25 µg/ml BSA, 0.5 mM ATP, 0.5 mM UTP, 0.5 mM CTP, 0.2 mM GTP, 1 mM 7-Me GpppG (Pharmacia, Piscataway, N.J.), 50–100 units RNA polymerase and 125–250 units RNasin (Promega, Madison, Wis.). The reactions were incubated at 40° C. for 90 minutes, treated with FPLC purified DNase (Pharmacia, Piscataway, N.J.), phenol extracted twice, ethanol precipitated twice, and then resuspended in 5–10 µl H$_2$O. See Julius, et al. Science 1988; 241:558–564, which is hereby incorporated by reference.

To measure bombesin-induced changes in intracellular calcium, the procedure described in Sandberg, et al. FEBS Lett 1988; 241:177–180 (hereby incorporated by reference) was followed with some modifications (see Spindel, et al., Mol. Endocrinol. 1990; 4:1956–1963; and Giladi, et al., Biotechniques 1991; 10:744–747) to determine, both of which are hereby incorproated by reference). More specifically, oocytes were removed from an albino Xenopus, treated with collagenase, defollicated, and then injected in the presence of OR-2 (a buffer solution suitable for frog oocytes) without calcium. The injection needles were rinsed with 1 mM EDTA before each use. For injection, the transcribed RNA (typically, 1–2 µl) was dried down and then suspended in an equal volume of an aequorin solution. The aequorin solution was prepared at a concentration of 1 mg/ml in 1 mM EDTA and stored in aliquots at −85° C. Aequorin was obtained from Friday Harbor Photoproteins, Friday Harbor, Wash.

To record the bombesin-induced response, oocytes were placed in 500 µl OR-2 in 12×55 mm disposable polystyrene tubes in a luminometer. Light output from the oocyte as recorded by the luminometer is a function of ligand-induced increases in intracellular calcium. The baseline response to OR-2 was first recorded, followed by the recording of the response to bombesin.

As a positive control, Xenopus oocytes containing exogenous human GRP receptor were also prepared and assayed in analogous manners.

FIG. 2 demonstrates the respective responses of GRP and BB4 receptors to 1 nM (in the OR-2 buffer) of bombesin. It is clear that the BB4 receptor, unlike the BRS-3 receptor, potently responded to bombesin.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

For example, contemplated equivalents of this invention include nucleic acid or peptide sequences which are substantially identical to those clearly described above and explicitly claimed below. By "substantially identical" is meant a nucleic acid or peptide exhibiting at least 50%, preferably 85%, more preferably 90%, and most preferably 95% homology to a reference amino acid or nucleic acid sequence. For peptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: (i) glycine, alanine; (ii) valine, isoleucine, leucine; (iii) aspartic acid, glutamic acid, asparagine, glutamine; (iv) serine, threonine; (v) lysine, arginine; and (vi) phenylalanine, tyrosine.

Furthermore, nucleic acide and peptides which are allelic variations, natural mutants, and induced mutants are also within the scope of this invention.

Still other contemplated equivalents of this invention include peptides which are shorter than a receptor of this invention (e.g., a fragment thereof) which has at least one antigenic determinant that is immunologically reactive with an antigenic determinant of that receptor.

Other embodiments are also within the claims set forth below.

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 1563
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
CACGAGTGCA  AGCACTAAAC  CACCCTAGTG  CTGATGAGAG  CTGTGATTTC  TGGAGATACC    60

GAGTTTGTGG  ACATCAATTA  GGTTTCATTT  GTGGAACTTT  AATTGAGGTC  ACTTGTGTGC   120

TGCAATTCAT  GAACTTGAAA  CTGCTGAAGA  AGAAATTTGG  AACAACTGAA  TTTTATTTAG   180

ATTAAAAAAA  A ATG CCT GAA GGT TTT CAG TCA CTT AAC CAG ACA TTG CCA       230
              Met Pro Glu Gly Phe Gln Ser Leu Asn Gln Thr Leu Pro
              1               5                   10

TCT GCT ATA AGT AGC ATA GCT CAT TTG GAA TCC CTT AAT GAC AGT TTC         278
Ser Ala Ile Ser Ser Ile Ala His Leu Glu Ser Leu Asn Asp Ser Phe
    15              20                  25

ATT TTA GGT GCA AAG CAA AGT GAA GAT GTA TCC CCT GGG TTA GAA ATA         326
Ile Leu Gly Ala Lys Gln Ser Glu Asp Val Ser Pro Gly Leu Glu Ile
30              35                  40                  45

CTG GCT CTA ATT TCT GTC ACA TAT GCT GTT ATT ATT TCT GTC GGT ATC         374
Leu Ala Leu Ile Ser Val Thr Tyr Ala Val Ile Ile Ser Val Gly Ile
                50                  55                  60

CTT GGA AAC ACA ATA CTT ATA AAA GTA TTT TTT AAA ATC AAG TCA ATG         422
Leu Gly Asn Thr Ile Leu Ile Lys Val Phe Phe Lys Ile Lys Ser Met
            65                  70                  75

CAG ACT GTT CCT AAT ATT TTC ATC ACC AGC CTG GCT TTT GGA GAT CTT         470
Gln Thr Val Pro Asn Ile Phe Ile Thr Ser Leu Ala Phe Gly Asp Leu
        80                  85                  90

CTT CTA CTG CTG ACC TGC GTG CCA GTG GAC GCA TCT CGG TAT ATT GTG         518
Leu Leu Leu Leu Thr Cys Val Pro Val Asp Ala Ser Arg Tyr Ile Val
    95                  100                 105

GAC ACG TGG ATG TTT GGA AGA GCT GGC TGT AAG ATA ATT TCC TTC ATA         566
Asp Thr Trp Met Phe Gly Arg Ala Gly Cys Lys Ile Ile Ser Phe Ile
110                 115                 120                 125

CAG CTT ACC TCT GTC GGA GTG TCG GTG TTT ACT TTA ACT GTC CTC AGT         614
Gln Leu Thr Ser Val Gly Val Ser Val Phe Thr Leu Thr Val Leu Ser
                130                 135                 140

ACT GAC AGG TAC AGA GCC ATT GTG AAA CCC TTG CAA TTG CAG ACC TCA         662
Thr Asp Arg Tyr Arg Ala Ile Val Lys Pro Leu Gln Leu Gln Thr Ser
            145                 150                 155

GAT GCC GTT TTG AAG ACA TGT GGC AAA GCT GTT TGT GTT TGG ATC ATT         710
Asp Ala Val Leu Lys Thr Cys Gly Lys Ala Val Cys Val Trp Ile Ile
        160                 165                 170
```

```
TCC ATG CTC CTC GCT GCT CCA GAA GCT GTG TTC TCA GAT TTG TAT GAA   758
Ser Met Leu Leu Ala Ala Pro Glu Ala Val Phe Ser Asp Leu Tyr Glu
    175             180             185

TTT GGC AGC TCG GAA AAA AAT ACC ACT TTT GAA GCC TGT GCT CCA TAT   806
Phe Gly Ser Ser Glu Lys Asn Thr Thr Phe Glu Ala Cys Ala Pro Tyr
190             195             200             205

CCA GTC TCT GAA AAG ATT CTG CAA GAG ACA CAT TCC CTA ATA TGC TTC   854
Pro Val Ser Glu Lys Ile Leu Gln Glu Thr His Ser Leu Ile Cys Phe
            210             215             220

CTG GTA TTC TAC ATT GTT CCC CTG TCA ATC ATT TCT GCA TAT TAC TTC   902
Leu Val Phe Tyr Ile Val Pro Leu Ser Ile Ile Ser Ala Tyr Tyr Phe
        225             230             235

CTT ATT GCA AAA ACC CTG TAC AAA AGT ACT TTC AAC ATG CCT GCT GAA   950
Leu Ile Ala Lys Thr Leu Tyr Lys Ser Thr Phe Asn Met Pro Ala Glu
    240             245             250

GAG CAC ACT CAC GCC CGA AAA CAG ATA GAA TCG CGC AAA CGA GTG GCA   998
Glu His Thr His Ala Arg Lys Gln Ile Glu Ser Arg Lys Arg Val Ala
    255             260             265

AAA ACT GTG TTG GTG TTG GTG GCA TTG TTC GCA GTG TGC TGG TTG CCA  1046
Lys Thr Val Leu Val Leu Val Ala Leu Phe Ala Val Cys Trp Leu Pro
270             275             280             285

AAC CAC ATG CTC TAC TTG TAT CGA TCC TTC ACA TAT CAC TCC GCA GTG  1094
Asn His Met Leu Tyr Leu Tyr Arg Ser Phe Thr Tyr His Ser Ala Val
            290             295             300

AAT TCC TCT GCG TTT CAC CTG TCA GCC ACA ATC TTT GCG CGA GTA CTG  1142
Asn Ser Ser Ala Phe His Leu Ser Ala Thr Ile Phe Ala Arg Val Leu
        305             310             315

GCT TTG CGC AAT TCC TGC GTC AAC CCC TTC GCC CTC TAT TGG CTA AGC  1190
Ala Leu Arg Asn Ser Cys Val Asn Pro Phe Ala Leu Tyr Trp Leu Ser
    320             325             330

AAG AGC TTT AGG CAG CAT TTT AAA AAG CAA GTG TAT TGT TGT AAG ACT  1238
Arg Ser Phe Arg Gln His Phe Lys Lys Gln Val Tyr Cys Cys Lys Thr
    335             340             345

GAA CCT CTG CAT CCA ACA AAG TCC GAC CCA CAG CAG TAC CAT AAC TGG  1286
Glu Pro Leu His Pro Thr Lys Ser Asp Pro Gln Gln Tyr His Asn Trp
350             355             360             365

AAT TAC CGC TGT GAA AGG CAA CAT CCA GAT GTC TGAAATTAGC           1329
Asn Tyr Arg Cys Glu Arg Gln His Pro Asp Val
            370             375

ATTACATTAT TAAGTGCTTA CGATGTAAAG AAAGAGTGAC AGTGTCGCCA AATAAGTTAT 1389

AAAAAGTTTA TAAAACTTAC TGTAAACAAA AGATGGATAA AGTTTTGTT GCTGCATATT  1449

GACGTCTGTT TATTAAAAAT CCAGAGTATA AAGTTTTATT ACTACAAACA AAAAAATATA 1509

CCTCAACATT CTAACCACAA TTGAATTATT CATATATTAC CCTTATTTAT TCAG       1563
```

( 2 ) INFORMATION FOR SEQ ID NO: 2:

( i ) SEQUENCE CHARACTERISTICS:
        ( A ) LENGTH: 376
        ( B ) TYPE: amino acid
        ( C ) STRANDEDNESS: single
        ( D ) TOPOLOGY: Not Relevant ( x i ) SEQUENCE DESCRIPTION: SEQ ID NO: 2:

```
Met Pro Glu Gly Phe Gln Ser Leu Asn Gln Thr Leu Pro Ser Ala Ile
 1               5              10              15

Ser Ser Ile Ala His Leu Glu Ser Leu Asn Asp Ser Phe Ile Leu Gly
            20              25              30

Ala Lys Gln Ser Glu Asp Val Ser Pro Gly Leu Glu Ile Leu Ala Leu
        35              40              45
```

|     |     |     |     |     |     |     |     |     |     |     |     |     |
|---|---|---|---|---|---|---|---|---|---|---|---|---|
| Ile | Ser | Val | Thr | Tyr | Ala | Val | Ile | Ile | Ser | Val | Gly | Ile | Leu | Gly | Asn |
|     | 50  |     |     |     | 55  |     |     |     | 60  |     |     |     |
| Thr | Ile | Leu | Ile | Lys | Val | Phe | Phe | Lys | Ile | Lys | Ser | Met | Gln | Thr | Val |
| 65  |     |     |     | 70  |     |     |     | 75  |     |     |     | 80  |
| Pro | Asn | Ile | Phe | Ile | Thr | Ser | Leu | Ala | Phe | Gly | Asp | Leu | Leu | Leu | Leu |
|     |     |     |     | 85  |     |     |     | 90  |     |     |     | 95  |
| Leu | Thr | Cys | Val | Pro | Val | Asp | Ala | Ser | Arg | Tyr | Ile | Val | Asp | Thr | Trp |
|     |     | 100 |     |     |     | 105 |     |     |     | 110 |
| Met | Phe | Gly | Arg | Ala | Gly | Cys | Lys | Ile | Ile | Ser | Phe | Ile | Gln | Leu | Thr |
|     | 115 |     |     |     | 120 |     |     |     | 125 |
| Ser | Val | Gly | Val | Ser | Val | Phe | Thr | Leu | Thr | Val | Leu | Ser | Thr | Asp | Arg |
|     | 130 |     |     |     | 135 |     |     |     | 140 |
| Tyr | Arg | Ala | Ile | Val | Lys | Pro | Leu | Gln | Leu | Gln | Thr | Ser | Asp | Ala | Val |
| 145 |     |     |     | 150 |     |     |     | 155 |     |     |     | 160 |
| Leu | Lys | Thr | Cys | Gly | Lys | Ala | Val | Cys | Val | Trp | Ile | Ile | Ser | Met | Leu |
|     |     |     | 165 |     |     |     | 170 |     |     |     | 175 |
| Leu | Ala | Ala | Pro | Glu | Ala | Val | Phe | Ser | Asp | Leu | Tyr | Glu | Phe | Gly | Ser |
|     |     | 180 |     |     |     | 185 |     |     |     | 190 |
| Ser | Glu | Lys | Asn | Thr | Thr | Phe | Glu | Ala | Cys | Ala | Pro | Tyr | Pro | Val | Ser |
|     | 195 |     |     |     | 200 |     |     |     | 205 |
| Glu | Lys | Ile | Leu | Gln | Glu | Thr | His | Ser | Leu | Ile | Cys | Phe | Leu | Val | Phe |
|     | 210 |     |     |     | 215 |     |     |     | 220 |
| Tyr | Ile | Val | Pro | Leu | Ser | Ile | Ile | Ser | Ala | Tyr | Tyr | Phe | Leu | Ile | Ala |
| 225 |     |     |     | 230 |     |     |     | 235 |     |     |     | 240 |
| Lys | Thr | Leu | Tyr | Lys | Ser | Thr | Phe | Asn | Met | Pro | Ala | Glu | Glu | His | Thr |
|     |     |     | 245 |     |     |     | 250 |     |     |     | 255 |
| His | Ala | Arg | Lys | Gln | Ile | Glu | Ser | Arg | Lys | Arg | Val | Ala | Lys | Thr | Val |
|     |     |     | 260 |     |     |     | 265 |     |     |     | 270 |
| Leu | Val | Leu | Val | Ala | Leu | Phe | Ala | Val | Cys | Trp | Leu | Pro | Asn | His | Met |
|     |     | 275 |     |     |     | 280 |     |     |     | 285 |
| Leu | Tyr | Leu | Tyr | Arg | Ser | Phe | Thr | Tyr | His | Ser | Ala | Val | Asn | Ser | Ser |
|     | 290 |     |     |     | 295 |     |     |     | 300 |
| Ala | Phe | His | Leu | Ser | Ala | Thr | Ile | Phe | Ala | Arg | Val | Leu | Ala | Leu | Arg |
| 305 |     |     |     | 310 |     |     |     | 315 |     |     |     | 320 |
| Asn | Ser | Cys | Val | Asn | Pro | Phe | Ala | Leu | Tyr | Trp | Leu | Ser | Arg | Ser | Phe |
|     |     |     | 325 |     |     |     | 330 |     |     |     | 335 |
| Arg | Gln | His | Phe | Lys | Lys | Gln | Val | Tyr | Cys | Cys | Lys | Thr | Glu | Pro | Leu |
|     |     | 340 |     |     |     | 345 |     |     |     | 350 |
| His | Pro | Thr | Lys | Ser | Asp | Pro | Gln | Gln | Tyr | His | Asn | Trp | Asn | Tyr | Arg |
|     |     | 355 |     |     |     | 360 |     |     |     | 365 |
| Cys | Glu | Arg | Gln | His | Pro | Asp | Val |
|     | 370 |     |     |     | 375 |

( 2 ) INFORMATION FOR SEQ ID NO: 3:

( i ) SEQUENCE CHARACTERISTICS:
        ( A ) LENGTH: 252
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
CAG  ACA  TCT  GAC  GCG  GTG  TTG  AAG  ACG  TGC  GGC  AAA  GCT  GTT  TGT  GTT      48
Gln  Thr  Ser  Asp  Ala  Val  Leu  Lys  Thr  Cys  Gly  Lys  Ala  Val  Cys  Val
 1                 5                        10                       15

TGG  ATT  ATC  TCC  ATG  CTA  CTT  GCT  GCC  CCT  GAG  GCA  GTG  TTT  TCG  GAT      96
```

```
             Trp  Ile  Ile  Ser  Met  Leu  Leu  Ala  Ala  Pro  Glu  Ala  Val  Phe  Ser  Asp
                            20                      25                      30

TTG  TAT  GAA  TTC  ACC  AGC  CCT  GAC  AAG  AAT  ATG  TCC  TTC  AAA  ACA  TGT                 144
Leu  Tyr  Glu  Phe  Thr  Ser  Pro  Asp  Lys  Asn  Met  Ser  Phe  Lys  Thr  Cys
          35                      40                      45

GCC  CCT  TAT  CCT  GTT  TCT  GAA  AAG  CTA  CTG  CAA  GAG  ACA  CAT  TCG  CTG                 192
Ala  Pro  Tyr  Pro  Val  Ser  Glu  Lys  Leu  Leu  Gln  Glu  Thr  His  Ser  Leu
     50                      55                      60

ATG  TGC  TTC  TTA  GTG  TTC  TAT  ATT  ATT  CCC  TTG  TCT  ATT  ATC  TCC  GCC                 240
Met  Cys  Phe  Leu  Val  Phe  Tyr  Ile  Ile  Pro  Leu  Ser  Ile  Ile  Ser  Ala
65                       70                      75                       80

TAC  TAC  TTC  CTC                                                                              252
Tyr  Tyr  Phe  Leu
               84
```

( 2 ) INFORMATION FOR SEQ ID NO: 4:

( i ) SEQUENCE CHARACTERISTICS:
        ( A ) LENGTH: 84
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 4:

```
Gln  Thr  Ser  Asp  Ala  Val  Leu  Lys  Thr  Cys  Gly  Lys  Ala  Val  Cys  Val
 1                   5                       10                      15

Trp  Ile  Ile  Ser  Met  Leu  Leu  Ala  Ala  Pro  Glu  Ala  Val  Phe  Ser  Asp
               20                       25                      30

Leu  Tyr  Glu  Phe  Thr  Ser  Pro  Asp  Lys  Asn  Met  Ser  Phe  Lys  Thr  Cys
          35                      40                      45

Ala  Pro  Tyr  Pro  Val  Ser  Glu  Lys  Leu  Leu  Gln  Glu  Thr  His  Ser  Leu
     50                      55                      60

Met  Cys  Phe  Leu  Val  Phe  Tyr  Ile  Ile  Pro  Leu  Ser  Ile  Ile  Ser  Ala
65                       70                      75                       80

Tyr  Tyr  Phe  Leu
               84
```

( 2 ) INFORMATION FOR SEQ ID NO: 5:

( i ) SEQUENCE CHARACTERISTICS:
        ( A ) LENGTH: 250
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
CAG  ACC  TCA  GAT  GCT  GTG  CTG  AAG  ACC  TGT  GCC  AAA  GCT  GGT  GGC  ATC                  48
Gln  Thr  Ser  Asp  Ala  Val  Leu  Lys  Thr  Cys  Ala  Lys  Ala  Gly  Gly  Ile
 1                   5                       10                      15

TGG  ATC  ATG  GCT  ATG  ATA  TTT  GCT  CTG  CCA  GAG  GCT  ATA  TTC  TCA  AAT                  96
Trp  Ile  Met  Ala  Met  Ile  Phe  Ala  Leu  Pro  Glu  Ala  Ile  Phe  Ser  Asn
               20                       25                      30

GTA  TAC  ACT  TTC  CAA  GGT  CCT  AAC  AGA  AAC  GTA  ACA  TTT  GAA  TCC  TGT                 144
Val  Tyr  Thr  Phe  Gln  Gly  Pro  Asn  Arg  Asn  Val  Thr  Phe  Glu  Ser  Cys
          35                      40                      45

AAC  TCC  TAC  CCT  ATC  TCT  GAG  AGG  CTT  TTG  CAG  GAA  ATA  CAT  TCT  CTG                 192
Asn  Ser  Tyr  Pro  Ile  Ser  Glu  Arg  Leu  Leu  Gln  Glu  Ile  His  Ser  Leu
     50                      55                      60

TTG  TGT  TTC  TTG  GTG  TTC  TAC  ATT  ATC  CCG  CTC  TCG  ATT  ATC  TCC  GCC                240
Leu  Cys  Phe  Leu  Val  Phe  Tyr  Ile  Ile  Pro  Leu  Ser  Ile  Ile  Ser  Ala
65                       70                      75                       80

TAT  TAC  TTC  C                                                                                250
```

Tyr Tyr Phe
         83

( 2 ) INFORMATION FOR SEQ ID NO: 6:

( i ) SEQUENCE CHARACTERISTICS:
            ( A ) LENGTH: 83
            ( B ) TYPE: amino acid
            ( C ) STRANDEDNESS: Not Relevant
            ( D ) TOPOLOGY: Not Relevant ( x i ) SEQUENCE DESCRIPTION: SEQ ID NO: 6:

Gln Thr Ser Asp Ala Val Leu Lys Thr Cys Ala Lys Ala Gly Gly Ile
 1           5                    10                    15

Trp Ile Met Ala Met Ile Phe Ala Leu Pro Glu Ala Ile Phe Ser Asn
             20                  25                  30

Val Tyr Thr Phe Gln Gly Pro Asn Arg Asn Val Thr Phe Glu Ser Cys
         35                  40                  45

Asn Ser Tyr Pro Ile Ser Glu Arg Leu Leu Gln Glu Ile His Ser Leu
     50                  55                  60

Leu Cys Phe Leu Val Phe Tyr Ile Ile Pro Leu Ser Ile Ile Ser Ala
 65                  70                  75                  80

Tyr Tyr Phe
         83

( 2 ) INFORMATION FOR SEQ ID NO: 7:

( i ) SEQUENCE CHARACTERISTICS:
            ( A ) LENGTH: 29
            ( B ) TYPE: nucleic acid
            ( C ) STRANDEDNESS: single
            ( D ) TOPOLOGY: linear ( i x ) FEATURE:
            ( D ) OTHER INFORMATION: N at each of positions 9, 12, 15,
                    18, 21, 24 and 27 is deoxyinosine ( x i ) SEQUENCE DESCRIPTION: SEQ ID NO: 7:

ATHCARCTNA CNTCNGTNGG NGTNTCNGT                                          29

( 2 ) INFORMATION FOR SEQ ID NO: 8:

( i ) SEQUENCE CHARACTERISTICS:
            ( A ) LENGTH: 30
            ( B ) TYPE: nucleic acid
            ( C ) STRANDEDNESS: single
            ( D ) TOPOLOGY: linear ( i x ) FEATURE:
            ( D ) OTHER INFORMATION: N at each of positions 4, 7, 13, 19
                    and 25 is deoxyinosine ( x i ) SEQUENCE DESCRIPTION: SEQ ID NO: 8:

RTANAGNGCR AANGGRTTNA CRCANGARTT                                         30

( 2 ) INFORMATION FOR SEQ ID NO: 9:

( i ) SEQUENCE CHARACTERISTICS:
            ( A ) LENGTH: 17
            ( B ) TYPE: nucleic acid
            ( C ) STRANDEDNESS: single
            ( D ) TOPOLOGY: linear ( i x ) FEATURE:
            ( D ) OTHER INFORMATION: N at each of positions 3, 9, 12 and
                    15 is A, C, G or T ( x i ) SEQUENCE DESCRIPTION: SEQ ID NO: 9:

MGNAARMGN Y TNGCNAA            17

(2) INFORMATION FOR SEQ ID NO: 10:

(i) SEQUENCE CHARACTERISTICS:
        (A) LENGTH: 17
        (B) TYPE: nucleic acid
        (C) STRANDEDNESS: single
        (D) TOPOLOGY: linear (ix) FEATURE:
        (D) OTHER INFORMATION: N at each of positions 3, 9, 12 and 15 is A, C, G or T (xi) SEQUENCE DESCRIPTION: SEQ ID NO: 10:

CCNACRAANA CNARNAC            17

What is claimed is:

1. A purified nucleic acid encoding a receptor for a bombesin-like peptide, said receptor comprising SEQ ID NO: 2.

2. The nucleic acid of claim 1, wherein said nucleic acid is genomic DNA.

3. The nucleic acid of claim 1, wherein said nucleic acid is cDNA.

4. The nucleic acid of claim 1, wherein said nucleic acid is RNA.

5. A vector comprising the nucleic acid of claim 1 for expression of the receptor encoded by said nucleic acid.

6. A cell into which the nucleic acid of claim 1 has been introduced.

7. A purified nucleic acid which hybridizes to the full length complement of the DNA sequence as set forth in SEQ ID NO: 1 under high-stringency hybridization conditions; and encodes a receptor protein for a bombesin-like peptide, wherein said receptor protein is expressed in the tissues of vertebrates.

8. A vector comprising the nucleic acid of claim 7 for expression of the receptor encoded by said nucleic acid.

9. A cell into which the nucleic acid of claim 7 has been introduced.

10. The nucleic acid of claim 7, wherein said nucleic acid is genomic DNA.

11. The nucleic acid of claim 7, wherein said nucleic acid is cDNA.

12. The nucleic acid of claim 7, wherein said nucleic acid is RNA.

* * * * *